United States Patent [19]

Lawson et al.

[11] Patent Number: 5,792,820
[45] Date of Patent: *Aug. 11, 1998

[54] ALKYLLITHIUM COMPOUNDS CONTAINING CYCLIC AMINES AND THEIR USE IN POLYMERIZATION

[75] Inventors: David F. Lawson, Uniontown; Thomas A. Antkowiak, Rittman; James E. Hall, Mogadore; Mark L. Stayer, Jr., Suffield; John R. Schreffler, Clinton, all of Ohio

[73] Assignee: Bridgestone Corporation, Tokyo, Japan

[*] Notice: The term of this patent shall not extend beyond the expiration date of Pat. No. 5,496,940.

[21] Appl. No.: 606,388

[22] Filed: Feb. 23, 1996

Related U.S. Application Data

[63] Continuation of Ser. No. 382,477, Feb. 1, 1995, Pat. No. 5,496,940.

[51] Int. Cl.$^6$ .................... C07D 223/06; C07D 227/06; C08F 4/48
[52] U.S. Cl. .................... 526/180; 526/204; 526/217; 540/450; 540/465; 540/482; 540/484; 540/541; 540/605; 540/612
[58] Field of Search .................... 540/450, 465, 540/482, 484, 541, 605, 612; 252/182.13, 182.14; 526/180, 204, 217

[56] References Cited

U.S. PATENT DOCUMENTS

| | | | |
|---|---|---|---|
| 2,849,432 | 8/1958 | Kibler et al. | 260/94.2 |
| 3,109,871 | 11/1963 | Zalinski et al. | 260/85.1 |
| 3,177,190 | 4/1965 | Hsieh | 260/94.2 |
| 3,178,398 | 4/1965 | Strobel et al. | 260/85.1 |
| 3,240,772 | 3/1966 | Natta et al. | 260/88.7 |
| 3,290,277 | 12/1966 | Anderson et al. | 260/88.2 |
| 3,317,918 | 5/1967 | Foster | 260/83.7 |
| 3,326,881 | 6/1967 | Uraneck et al. | 260/94.6 |
| 3,331,821 | 7/1967 | Strobel | 260/83.7 |
| 3,393,182 | 7/1968 | Trepka | 260/79.5 |
| 3,426,006 | 2/1969 | Nützel et al. | 260/83.5 |
| 3,439,049 | 4/1969 | Trepka | 260/624 |
| 3,856,877 | 12/1974 | Otsuki et al. | 260/677 R |
| 3,935,177 | 1/1976 | Müller et al. | 260/84.7 |
| 4,015,061 | 3/1977 | Schulz et al. | 526/178 |
| 4,026,865 | 5/1977 | Uraneck et al. | 260/42.32 |
| 4,085,265 | 4/1978 | Otsuki et al. | 526/49 |
| 4,247,418 | 1/1981 | Halasa et al. | 252/431 N |
| 4,316,001 | 2/1982 | Boileau et al. | 528/14 |
| 4,383,085 | 5/1983 | Fujimaki et al. | 525/196 |
| 4,414,372 | 11/1983 | Farnham et al. | 526/190 |
| 4,429,091 | 1/1984 | Hall | 526/181 |
| 4,476,240 | 10/1984 | Hall et al. | 502/155 |
| 4,478,953 | 10/1984 | Yuki et al. | 502/155 |
| 4,515,922 | 5/1985 | Sakakibara et al. | 525/99 |
| 4,614,771 | 9/1986 | Watanabe et al. | 525/351 |
| 4,616,069 | 10/1986 | Watanabe et al. | 525/370 |
| 4,647,634 | 3/1987 | Jalics | 526/174 |
| 4,677,153 | 6/1987 | Kitahara et al. | 524/552 |
| 4,734,461 | 3/1988 | Roggero et al. | 525/293 |
| 4,735,994 | 4/1988 | Rogger et al. | 525/279 |
| 4,736,003 | 4/1988 | Schneider et al. | 526/190 |

(List continued on next page.)

FOREIGN PATENT DOCUMENTS

| | | | |
|---|---|---|---|
| 0 067 111 A2 | 5/1982 | European Pat. Off. | B60C 1/00 |
| 0 180 141 A1 | 10/1985 | European Pat. Off. | C08C 19/44 |
| 0 207 565 A1 | 6/1986 | European Pat. Off. | C08C 19/44 |
| 0 264 506 A1 | 10/1986 | European Pat. Off. | B60C 21/08 |
| 0 282 437 A2 | 3/1988 | European Pat. Off. | C08F 4/44 |
| 0 290 883 A1 | 4/1988 | European Pat. Off. | C08C 19/42 |
| 0 316 255 A2 | 10/1988 | European Pat. Off. | C08C 19/44 |
| 0 451 603 A2 | 3/1991 | European Pat. Off. | C08F 4/48 |
| 2 250 774 | 11/1974 | France | C08F 36/04 |
| 138 070 | 10/1979 | Germany | C08F 4/46 |
| 247455 | 3/1986 | Germany . | |
| 54-65788 | 5/1979 | Japan | C08F 4/52 |
| 59-164308 | 9/1984 | Japan | C08F 10/02 |
| 2 117 778 | 3/1983 | United Kingdom | C08C 19/42 |

OTHER PUBLICATIONS

"3–Dimethylaminopropyl–Lithium—An Analytical and Kinetic Investigation of a New Initiator System for Polymer Synthesis" by Eisenbach et al., *European Patent Journal*, vol. 11, pp. 699–704 (1975).

"A Bifunctional Anionic Initiator Soluble in Non–polar Solvents" by Beinert et al., *Makromol. Chem 179*, pp. 551–555 (1978).

(List continued on next page.)

*Primary Examiner*—Mukund J. Shah
*Assistant Examiner*—Deepak R. Rao
*Attorney, Agent, or Firm*—Daniel N. Hall

[57] ABSTRACT

An organolithium compound according to the present invention containing a cyclic amino group, has the general formula:

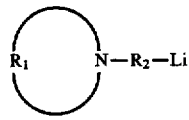

wherein $R_1$ is a divalent alkylene, an oxy- or amino-alkylene, or substituted alkylene having from 6 to about 20 carbon atoms; $R_2$ is a linear-, branched-, or cyclo-alkylene having from about 2 to about 20 carbon atoms; and the lithium, Li, is bonded directly to a carbon atom of $R_2$. A method of preparing an organolithium compound containing a cyclic amino group, comprising reacting a cyclic amino organo halide having the general formula

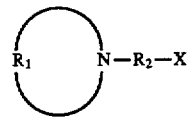

where $R_1$ and $R_2$ are as above, and X is bromine or chlorine bonded directly to a carbon atom of $R_2$, with a lithium reactant selected from lithium metal or an organolithium compound.

8 Claims, No Drawings

U.S. PATENT DOCUMENTS

| | | | |
|---|---|---|---|
| 4,791,174 | 12/1988 | Bronstert et al. | 525/274 |
| 4,816,520 | 3/1989 | Bronstert | 525/285 |
| 4,835,209 | 5/1989 | Kitagawa et al. | 524/507 |
| 4,843,120 | 6/1989 | Halasa et al. | 525/53 |
| 4,894,409 | 1/1990 | Shimada et al. | 524/492 |
| 4,914,147 | 4/1990 | Mouri et al. | 524/495 |
| 4,931,376 | 6/1990 | Ikematsu et al. | 526/164 |
| 4,935,471 | 6/1990 | Halasa et al. | 525/359.1 |
| 4,978,754 | 12/1990 | Ibi et al. | 544/176 |
| 5,066,729 | 11/1991 | Stayer, Jr. et al. | 525/315 |
| 5,112,929 | 5/1992 | Hall | 526/181 |
| 5,115,035 | 5/1992 | Shiraki et al. | 525/314 |
| 5,149,457 | 9/1992 | Smith | 252/182.12 |
| 5,153,159 | 10/1992 | Antkowiak et al. | 502/155 |
| 5,173,209 | 12/1992 | Smith, Jr. et al. | 252/182.14 |
| 5,238,893 | 8/1993 | Hergenrother et al. | 502/155 |
| 5,292,790 | 3/1994 | Shimizu et al. | 524/496 |
| 5,329,005 | 7/1994 | Lawson et al. | 540/450 |
| 5,332,810 | 7/1994 | Lawson et al. | 540/450 |
| 5,393,721 | 2/1995 | Kitamura et al. | 502/154 |
| 5,523,364 | 6/1996 | Engel et al. | 526/180 |
| 5,527,753 | 6/1996 | Engel et al. | 502/155 |
| 5,550,203 | 8/1996 | Engel et al. | 526/336 |

OTHER PUBLICATIONS

"An improved synthesis of p–dimethylaminophenyl–lithium" by Hallas et al., *Chemistry and Industry*, p. 620 (1969).

"Anionic Polymerization. VII Polymerization and Copolymerization with Lithium Nitrogen–Bonded Initiator" by Cheng, *American Chemical Society*, pp. 513–528 (1981).

"Anionic Polymerization Initiators Containing Protected Functional Groups and Functionally Terminated Diene Polymers" by Schulz et al., *Journal of Polymer Science: Polymer Chemistry Edition*, vol. 12, pp. 153–166 (1974).

"Anionic Polymerization Initiated by Diethylamide in Organic Solvents. I. The Use of Lithium Diethylamide as a Polymerization Catalyst and the Effect of Solvent Type on the Polymerization of Isoprene and Styrene" by Angood et al., *Journal of Polymer Science: Polymer Chemistry Edition*, vol. 11, pp. 2777–2791 (1973).

"Anionic Polymerization Initiators Containing Protected Functional Groups. II." by Schulz et al., *Journal of Polymer Science: Polymer Chemistry Edition*, vol. 15, pp. 2401–2410 (1977).

"Bifunctional anionic initiators: A critical study and overview" by Bandermann et al., *Makromol. Chem* 186, pp. 2017–2024 (1985).

"Butadiene–Styrene Copolymerization Initiated by n–BuLi/THF/t–AmOK", by Lehong et al., *Journal of Applied Polymer Science*, vol. 44, pp. 1499–1505 (1992).

"6001 Chemical Abstracts", vol. 91, p. 59 (1979).

"Copolymerization of Butadiene and Styrene by Initiation with Alkyllithium and Alkai Metal tert–Butoxides" by Wofford et al., *Journal of Polymer Science: Part A–1*, vol. 7, pp. 461–469 (1969).

"Lithium Amide Catalyzed Amine–Olefin Addition Reactions" by Schlott et al., *J. Org. Chem.*, vol. 37, No. 26, pp. 4243–4245 (1972).

"New perfectly difunctional organolithium initiators for block copolymer synthesis: Synthesis of dilithium initiators in the absence of polar additives", by Guyot et al., *Polymer*, vol. 22 (1981).

"Polymerization of Unsaturated Compounds in the Presence of Lithium Diethylamide" by Vinogradov et al., *Polymer Science U.S.S.R.*, vol. 4, pp. 1568–1572 (1963).

"Ortho Lithiation via a Carbonyl Synthon" by Harris et al., *J. Org. Chem.*, vol. 44, No. 12, pp. 2004–2006 (1979).

"Preparation and Reactions of Trialkyltinlithium" by Tamborski et al., pp. 237–239, Jan. 1963.

"Preparation of Some Trialkyltin–lithium Compounds" by Gilman et al., *J. Am. Chem. Soc.* 75, pp. 2507–2509 (1953).

"Some Reactions of Tributyl– and Triphenyl–stannyl Derivatives of Alkali Metals" by Blake et al., *J. Chem. Soc.*, pp. 618–622, (1961).

"Specific Functionalization of Polymers by Carboxyl Groups" by Broze et al., *Makromol. Chem.* 179, pp. 1383–1386 (1978).

"Stereospecific Addition Reaction Between Butadiene and Amines" by Imai et al., *Tetrahedron Letters No. 38*, pp. 3317–3520 (1971).

"Studies of the Anionic Polymerization of Phenyl Vinyl Sulfoxide and Its Copolymer with Styrene" by Kanga et al. *Macromolecules 23*, pp. 4235–4240 (1990).

"Synthesis of New Monomers by Addition Reactions of Diethylamine to 1,4–Divinylbenzene Catalyzed by Lithium Diethylamide" by Tsuruta et al., *Makromol. Chem.* 177, pp. 3255–3263 (1976).

"The Microstructure of Butadiene and Styrene Copolymers Sythesized with n–BuLi/THF/t–AmOK" by Lehong et al., *Journal of Applied Polymer Science*, vol. 44, pp. 1507–1511 (1992).

"Thermal Elimination of Poly(phenyl vinyl sulfoxide) and Its Polystyrene Block Copolymers" by Kanga et al., *Macromolecules 23*, pp. 4241–4246 (1990).

"Metalations of Benzyldimethylamine and Related Amines with n–Butyllithium in Ether. Deuteration to Form Ring and Side–chain Derivatives" by Jones et al., *J. Org. Chem. 23*, 663 (Mar. 1963) pp. 663–665.

ALKYLLITHIUM COMPOUNDS CONTAINING CYCLIC AMINES AND THEIR USE IN POLYMERIZATION

This application is a continuation of application Ser. No. 08/382,477, filed Feb. 1, 1995 now U.S. Pat. No. 5,496,940.

TECHNICAL FIELD

The subject invention relates to polymers made by anionic initiation with alkyllithium compounds containing cyclic amines, such as polymerizations of dienes and diene/comonomer mixtures resulting in diene polymer and copolymer elastomers. Polymers prepared with the compounds of the present invention exhibit improved characteristics such as for example, improved hysteresis loss characteristics, and reproducible, relatively narrow range molecular weight distributions.

BACKGROUND ART

When conducting polymerizations on a commercial basis, it is important to utilize process conditions and components which will allow the molecular weight of the end products to be narrowly and reproducibly defined. The characteristics of a given polymer and its usefulness, are dependent, among other things, upon its molecular weight. Hence, it is desirable to be able to predict with some certainty the molecular weight of the end product of the polymerization. When the molecular weight is not narrowly definable, or is not reproducible on a systematic basis, the process is at a commercial disadvantage.

Further, it is desirable to produce elastomeric compounds exhibiting improved characteristics such as reduced hysteresis loss characteristics. Such elastomers, when compounded to form articles such as tires, power belts and the like, will show an increase in rebound, a decrease in rolling resistance and less heat build-up when mechanical stresses are applied.

A major source of hysteretic power loss has been established to be due to the section of the polymer chain from the last cross link of the vulcanizate to the end of the polymer chain. This free end cannot be involved in an efficient elastic recovery process, and as a result, any energy transmitted to this section of the cured sample is lost as heat. It is known in the art that this type of mechanism can be reduced by preparing higher molecular weight polymers which will have fewer end groups. However, this procedure is not useful because processability of the rubber with compounding ingredients and during shaping operations decreases rapidly with increasing molecular weight of the rubber.

The present invention provides polymers made by anionic initiation with novel alkyl lithium compounds containing cyclic amines. Use of the compounds of the present invention allows the incorporation of a functionality from the initiator to be incorporated at least at the head of the polymer chain. The initiators used in the invention not only provide for improved polymerizations, but also result in polymers having a relatively predictable, controllable and reproducible molecular weight range distribution. Because of the incorporated functionality, the polymers and products of the invention exhibit improved (that is, reduced) hysteresis loss characteristics.

Certain aminoalkyllithium compounds are known in the art. For example, U.S. Pat. No. 4,935,471 discloses dialkylamino oligoalkenyl lithiums including piperidinyl and pyrrolidinyl oligoalkenyl lithiums. It has been found that when compounded with conventional vulcanizable rubber components, some of these materials do not interact effectively with carbon black. Others possess an odor which makes their commercial use undesirable. The present invention provides polymers derived from aminoalkyllithium compounds with improved interaction with carbon black and which do not have the objectionable odor associated with the piperidinyl and pyrrolidinyl compounds.

DISCLOSURE OF THE INVENTION

It is therefore, an object of the present invention to provide anionic polymerization initiators.

It is a further object of the present invention to provide a method of preparing such anionic polymerization initiators.

It is still a further object of the invention to provide an initiator which will reproducibly result in a polymer within a narrow, predictable molecular weight range.

It is an additional object of the invention to provide an initiator which will allow for the incorporation of a functional group at least at the head of the resulting polymer.

It is another object of the present invention to provide methods of using such polymerization initiators to form improved elastomers.

It is yet another object of the present invention to use such initiators to provide elastomers having a plurality of polymer molecules wherein substantially each molecule has a functional group from the initiator.

It is also an object of certain embodiments of the present invention to provide anionic initiators which will produce diene polymers and copolymers having reduced hysteresis characteristics.

At least one or more of these objects together with the advantages thereof over the existing art, which shall become apparent from the specification which follows, are accomplished by the invention as hereinafter described and claimed.

In general, the present invention relates to alkyl lithium compounds containing cyclic amines, comprising the general formula:

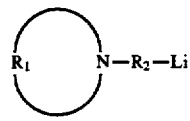

wherein $R_1$ is a divalent alkylene, an oxy- or aminoalkylene, or substituted alkylene having from 6 to about 20 carbon atoms; $R_2$ is a linear-, branched-, or cyclo-alkylene having from about 2 to about 20 carbon atoms; and, Li is a lithium atom bonded directly to a carbon atom of $R_2$. The compound may be useful, for example, as an anionic polymerization initiator. The resulting polymers and compounds formed therefrom exhibit improvements such as reduced hysteresis loss characteristics.

A method of preparing a cyclic amine compound according to the invention comprises reacting a cyclic amino halide having the general formula

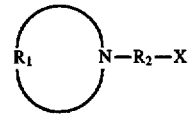

wherein $R_1$ and $R_2$ are as defined above and X is chlorine or bromine, with a lithium reactant selected from the group consisting of elemental lithium metal and RLi wherein R is selected from the group consisting of alkyls, cycloalkyls, alkenyls, aryls and aralkyls having from 1 to about 20 carbon atoms and short chain length low molecular weight polymers from diolefin and vinyl aryl monomers having up to about 25 units.

Another embodiment of a cyclic amine compound according to the invention has the general formula $R_4R_2Li$, where $R_2$ is as defined above, and $R_4$ is a cyclic amino radical having the general formula

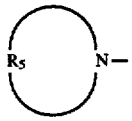

where $R_5$ is selected from the group consisting of a divalent alkylene, an oxy- or amino-alkylene, and a substituted alkylene having from 4 to about 20 carbon atoms, a substituted nitrogen having the general formula $R_6N$ where $R_6$ is selected from the group consisting of an alkyl having from 1 to about 12 carbon atoms; a cycloalkyl having from about 5 to about 20 carbon atoms; an aryl having from about 6 to about 20 carbon atoms; and, an aralkyl having from 7 to about 20 carbon atoms; and mixtures thereof, with the limitation that $R_4$ has from 2 to about 4 nitrogen atoms and a total of from 6 to about 24 atoms in the ring structure thereof.

Use of the anionic initiators of the invention provides a functionalized polymer which comprises a polymer molecule having the general formula AYLi where A is a cyclic amine-containing radical having the general formula

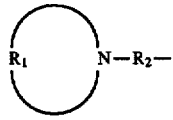

wherein $R_1$ and $R_2$ are as discussed hereinabove; Y is a divalent polymer radical; and the lithium atom, Li, is bonded directly to a carbon atom of Y.

A functionalized polymer made from the anionic initiator of the present invention also comprises a polymer molecule having the general formula AYLi where A is a cyclic amine-containing radical having the general formula

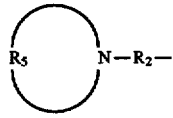

wherein A, $R_2$, $R_5$ and Y are as discussed hereinabove.

The initiators of the present invention can also be used in a method of preparing a polymer which comprises preparing a solution of 1 or more anionically polymerizable monomers in a solvent; and, polymerizing under effective conditions, the monomers in the presence of a polymerization initiator according to the present invention and having the general formula

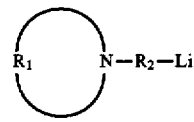

wherein $R_1$, $R_2$ and Li are as discussed hereinabove.

A method for preparing a polymer using the anionic initiators of the present invention comprises preparing a solution of 1 or more anionically polymerizable monomers in a solvent; and polymerizing under affective conditions, the monomers in the presence of a polymerization initiator according to the present invention and having the general formula

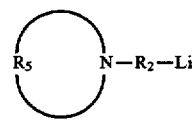

wherein $R_2$, $R_5$ and Li are as discussed hereinabove.

PREFERRED EMBODIMENT FOR CARRYING OUT THE INVENTION

As will become apparent from the description which follows, the present invention provides novel aminoalkyllithium compounds useful for example, as anionic polymerization initiators for the preparation of diene polymer and copolymer elastomers. It has been discovered herein that certain vulcanizable elastomeric compounds and articles thereof based upon such polymers formed using such initiators, exhibit useful properties, such as for example, reproducible relatively narrow molecular weight ranges. Furthermore, such polymers also contain a functionality from the initiator, which functionality is useful for example, in reducing hysteresis loss characteristics in the resulting polymers.

The preferred aminoalkyllithium compound according to the invention contains a cyclic amine. The preferred initiator is therefore, an amine having the general formula ALi, wherein the component "A" represents the cyclic amine functionality to be incorporated at the initiation site or the head of the resulting polymer when the inventive amine compound is employed as an initiator. "A" is preferably a cyclic amine radical having the general formula (I)

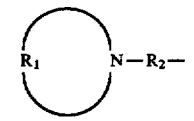

wherein $R_1$ is a divalent alkylene, oxy- or amino-alkylene, or substituted alkylene moiety having from 6 to about 20 carbon atoms, more preferably from 6 to 12 carbon atoms; and, $R_2$ is a linear-, branched-, or cyclo-alkylene moiety having from about 2 to about 20 carbon atoms, and more preferably, from 3 to 12 carbon atoms. The lithium atom, Li, is bonded directly to a carbon atom of A.

Examples of $R_1$ include hexamethylene, heptamethylene, dodecamethylene and hexadecamethylene moieties and the like. Examples of preferred R2 groups have from about 3 to about 6 carbon atoms and include propyl and hexyl moieties and the like. Hence, examples of preferred cyclic amino compounds according to the invention include hexamethyleneiminopropyllithium.

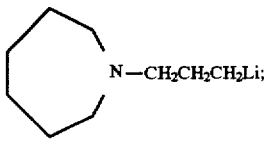

hexamethyleneiminohexyllithium,

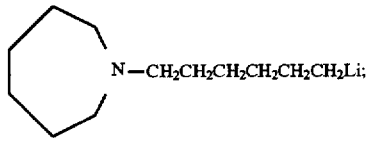

and, dodecamethyleneiminopropyllithium

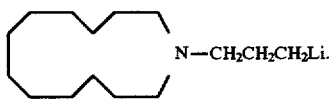

The carbon and nitrogen atoms in the cyclic amine ring structure of "A" can also be substituted, such that the aminoalkyllithium of this embodiment has the general formula

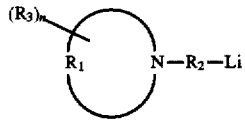

wherein $R_3$ is a tertiary amino or an alkyl group having from about 1 to about 12 carbon atoms; an aryl having from about 6 to about 20 carbon atoms; an aralkyl having from about 7 to about 20 carbon atoms; an alkenyl having from about 2 to about 12 carbon atoms; a cycloalkyl having from about 5 to about 20 carbon atoms; a cycloalkenyl having from about 5 to about 20 carbon atoms; a bicycloalkyl having from about 6 to about 20 carbon atoms; or, a bicycloalkenyl having from about 6 to about 20 carbon atoms; where n is an integer of from about 1 to about 10. The O-, S- or N-containing analogs of $R_3$, which analogs are substantially non-reactive with the alkyllithium of the cyclic amino compound, are also within the scope of the invention. By "analog" it is meant a compound in which one or more O, S and/or N atoms may replace one or more carbon atoms. The lithium atom, Li, is bonded directly to a carbon atom in $R_2$.

Further, $R_2$ can be a branched- or cyclo-alkylene in addition to being a linear-alkylene as discussed hereinabove. Examples of branched-alkylene-containing (lithio)alkyl portions include 2,2-dimethylpropane-1,3-diyl; 2-methylpropane-1,3-diyl; 2-methylbutane-1,4diyl; and 2-2-dimethyloctane-1,8-diyl. Examples of cyclo-alkylene (lithio)alkyl portions include cyclohexane-1,4-diyl; cyclohexane-1,3-diyl; cyclododecane-1,7-diyl; cyclooctane-1,3-diyl; and, cyclohexadecane-1,5-diyl.

According to another embodiment of the present invention, the cycloalkyl amine portion of "A" has at least seven ring atoms therein, including about 2 to about 4 amine nitrogens. Such a cyclic amine compound has the general formula $R_4R_2Li$ where $R_2$ is as defined above, and $R_4$ is a cyclic amino radical having the general formula

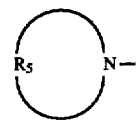

where $R_5$ is selected from the group consisting of a divalent alkylene, an oxy- or amino-alkylene, and a substituted alkylene having from 4 to about 20 carbon atoms, a substituted nitrogen having the general formula $R_6N$ where $R_6$ is selected from the group consisting of an alkyl having from 1 to about 12 carbon atoms; a cycloalkyl having from about 5 to about 20 carbon atoms; an aryl having from about 6 to about 20 carbon atoms; and, an aralkyl having from 7 to about 20 carbon atoms; and mixtures thereof, with the limitation that $R_4$ has from 2 to about 4 nitrogen atoms and a total of from 6 to about 24 atoms in the ring structure thereof. The cyclic amine initiator according to the invention can thus have the following general formula, where $R_5$, $R_2$ and Li are as described hereinabove:

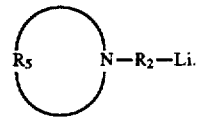

The atoms in $R_5$ can be substituted in the same manner as described above, that is, with "A" being substituted with $(R_3)n$.

Therefore, in addition to formula (I) hereinabove, "A" can also be a cyclic amine radical having the general formula (II) $R_4R_2$— where $R_4$ and $R_2$ are as described hereinabove.

Therefore, according to the present invention, in the alkyl lithium compounds containing cyclic amines, the size of the ring in the cyclic amine portion is greater than or equal to 7 atoms when there is only one nitrogen atom in the ring, or greater than or equal to 6 atoms when there are 2 or more nitrogen atoms in the ring.

Examples of amine compounds having the structure $R_4R_2Li$ as above are mono-N alkyl or N-aryl derivatives or piperazines; mono N-alkyl derivatives of homopiperazine (1,4-diazacycloheptanes); mono-N-alkyl derivatives of 1,4- or 1,5-diazacyclooctanes, and ring C-substituted 1,4- or 1,5-diazacyclooctanes and the like. Ring C-substituted N-alkylpiperazines are also within the scope of the invention. Substituted triaza ring systems are also included within $R_4$-.

The initiator used in the present invention can be formed by any number of techniques. One preferred method of preparing a cyclic amine compound according to the invention is to react a cyclic aminoalkyl halide with a lithio reactant selected from elemental lithium metal, an organolithium compound, and mixtures thereof. The aminoalkyl halide has the general formula AX where A is as defined by formulas I or II hereinabove, and X is a halogen selected from bromine, chlorine, iodine or the like, preferably bromine or chlorine, and wherein X is bonded directly to a carbon atom of $R_2$ in either formula I or II. The preparation of cyclic aminoalkyl halides is known to the art.

When reacted with elemental lithium metal in a suitable solvent such as hexane, cyclohexane, benzene or the like, the resulting reduction reaction produces a lithiated cyclic amine compound ALi where "A" is as defined hereinabove and the lithium atom, Li, is directly bonded to a carbon atom of A. The lithiated cyclic amine compound ALi can be complexed with one or more ligand molecules (such as THF) which help stabilize it but do not otherwise affect the reaction.

In the alternative, the amino reactant AX can also be reacted with an organolithium reactant having the general formula RLi, again in a suitable solvent such as those described hereinabove. RLi can be for example, selected from the group consisting of alkyls, cycloalkyls, alkenyls, aryls and aralkyls having from 1 to about 20 carbon atoms and short chain length low molecular weight polymers from diolefin and vinyl aryl monomers having up to about 25 units. Typical alkyls include n-butyl, s-butyl, t-butyl, methyl, ethyl, isopropyl and the like. The cycloalkyls include cyclohexyl, menthyl and the like. The alkenyls include allyl, vinyl and the like. The aryl and aralkyl groups include phenyl, benzyl, oligo(styryl) and the like. Exemplary short chain length polymers include the oligo(butadienyls), oligo (isoprenyls), oligo(styryls) and the like. Alkyllithium reactants such as t-butyl lithium are preferred.

The two components are allowed to react for up to about twenty-four hours at low to ambient temperature (−70° to 30° C.), or elevated temperatures up to about 100° C., preferably at less than 50° C., and more preferably at less than 38° C.

If one atom equivalent of lithium in the organolithium reactant is used per atom equivalent of AX, a byproduct of the reaction will be an organo halide (that is, RX) which may be undesirable for the intended use of the inventive compound. It may therefore, be preferable to employ two or more atom equivalents of lithium from the organolithium reactant per atom equivalent of AX. It is believed that a reaction with the excess of lithium will result in a lithium halide and other low molecular weight hydrocarbon by-products, which may be more acceptable for the intended use of the inventive initiator material.

As stated above, the compound ALi or $R_4R_2Li$ thus formed may be employed as an initiator to prepare any anionically-polymerized elastomer, e.g., polybutadiene, polyisoprene and the like, and copolymers thereof with monovinyl aromatics such as styrene, alpha methyl styrene and the like, or trienes such as myrcene. Thus, the elastomers include diene homopolymers and copolymers thereof with monovinyl aromatic polymers. Suitable monomers include conjugated dienes having from about 4 to about 12 carbon atoms and monovinyl aromatic monomers having 8 to 18 carbon atoms and trienes. Examples of conjugated diene monomers and the like useful in the present invention include 1,3-butadiene, isoprene, 1,3-pentadiene, 2,3-dimethyl-1,3-butadiene and 1,3-hexadiene, and aromatic vinyl monomers include styrene, alpha-methylstyrene, p-methylstyrene, vinyltoluene and vinylnaphthalene. The conjugated diene monomer and aromatic vinyl monomer are normally used at the weight ratios of 95-50:5-50, preferably 95-65:5-35.

Polymerization is conducted in polar or non-polar solvent, such as tetrahydrofuran (THF), a hydrocarbon solvent, such as the various cyclic and acyclic hexanes, heptanes, octanes, pentanes, their alkylated derivatives, and mixtures thereof. In order to promote randomization in copolymerization and to control vinyl content, a polar coordinator may be added to the polymerization ingredients. Amounts range between 0 and 90 or more equivalents per equivalent of lithium. The amount depends on the amount of vinyl desired, the level of styrene employed and the temperature of the polymerization, as well as the nature of the specific polar coordinator (modifier) employed. Suitable polymerization modifiers include for example, ethers or amines to provide the desired microstructure and randomization of the comonomer units. The molecular weight of the polymer ("base polymer") that is produced in this invention is optimally such that a proton-quenched sample will exhibit a gum Mooney (ML/4/100)) of from about 1 to about 150. However, useful lower molecular weight compounds can also be made using these initiators. These might typically be considered fluids, having molecular weights ranging from several hundreds to tens of thousands of mass units.

Other compounds useful as polar coordinators are organic and include tetrahydrofuran (THF), linear and cyclic oligomeric oxolanyl alkanes such as 2,2-bis(2'-tetrahydrofuryl) propane, di-piperidyl ethane, dipiperidyl methane, hexamethylphosphoramide, N-N'-dimethylpiperazine, diazabicyclooctane, dimethyl ether, diethyl ether, tributylamine and the like. The linear and cyclic oligomeric oxolanyl alkane modifiers are described in U.S. Pat. No. 4,429,091, owned by the Assignee of record, the subject matter of which relating to such modifiers is incorporated herein by reference. Compounds useful as polar coordinators include those having an oxygen or nitrogen hetero-atom and a non-bonded pair of electrons. Other examples include dialkyl ethers of mono and oligo alkylene glycols; "crown" ethers; tertiary amines such as tetramethylethylene diamine (TMEDA); linear THF oligomers; and the like.

A batch polymerization is begun by charging a blend of monomer(s) and normal alkane solvent to a suitable reaction vessel, followed by the addition of the polar coordinator (if employed) and the initiator compound previously described. The reactants are heated to a temperature of from about 20 to about 200° C., and the polymerization is allowed to proceed for from about 0.1 to about 24 hours. A functional amine group is derived from the initiator compound and attaches at the initiation site. Thus, substantially every resulting polymer molecule can be represented by the following general formula

AYLi where A is as described above, and Y is a divalent polymer radical which is derived from any of the foregoing diene homopolymers, monovinyl aromatic polymers, diene/monovinyl aromatic random copolymers and block copolymers. The monomer addition at the lithium end causes the molecular weight of the polymer to increase as the polymerization continues.

To terminate the polymerization, and thus further control polymer molecular weight, a terminating agent, coupling agent or linking agent may be employed, all of these agents being collectively referred to herein as "terminating reagents". Certain of these reagents may provide the resulting polymer with a multifunctionality. That is, the polymers initiated according to the present invention, may carry at least one amine functional group A as discussed hereinabove, and may also carry a second functional group selected and derived from the group consisting of terminating reagents, coupling agents and linking agents.

Useful terminating, reagents include active hydrogen compounds such as water or alcohol; carbon dioxide; N,N, N',N'-tetradialkyldiamino-benzophenone (such as tetramethyidiaminobenzophenone or the like); N,N-dialkylaminobenzaldehyde (such as dimethylaminobenzaldehyde or the like); 1,3-dialkyl-2-imidazolidinones (such as 1,3-dimethyl-2-imidazolidinone or the like); 1-alkyl substituted pyrrolidinones; 1-aryl substituted pyrrolidinones; dialkyl- and dicycloalkyl-carbodiimides having from about 5 to about 20 carbon atoms; $(R_7)_aZX_b$;

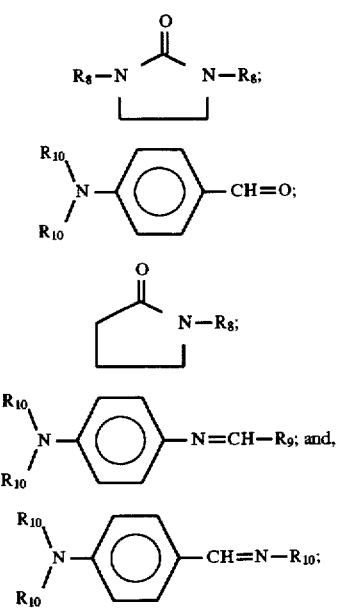

where Z is tin or silicon. It is preferred that Z is tin.

$R_7$ is an alkyl having from about 1 to about 20 carbon atoms; a cycloalkyl having from about 3 to about 20 carbon atoms; an aryl having from about 6 to about 20 carbon atoms; or, an aralkyl having from about 7 to about 20 carbon atoms. For example, $R_7$ may include methyl, ethyl, n-butyl, neophyl, phenyl, cyclohexyl or the like.

X is chlorine or bromine, "a" is from 0 to 3, and "b" is from about 1 to 4; where a+b=4.

Each $R_8$ is the same or different and is an alkyl, cycloalkyl or aryl, having from about 1 to about 12 carbon atoms. For example, $R_8$ may include methyl, ethyl, nonyl, t-butyl, phenyl or the like.

$R_9$ is an alkyl, phenyl, alkylphenyl or dialkylaminophenyl, having from about 1 to about 20 carbon atoms. For example, $R_9$ may include t-butyl, 2-methyl-4-pentene-2-yl, phenyl, p-tolyl, p-butylphenyl, p-dodecylphenyl, p-diethylaminophenyl, p-(pyrrolidino) phenyl, and the like.

Each $R_{10}$ is the same or different, and is an alkyl or cycloalkyl having from about 1 to about 12 carbon atoms. Two of the $R_{10}$ groups may together form a cyclic group. For example, $R_{10}$ may include methyl, ethyl, octyl, tetramethylene, pentamethylene, cyclohexyl or the like.

$R_{11}$ may include alkyl, phenyl, alkylphenyl or dialkylaminophenyl, having from about 1 to about 20 carbon atoms. For example, $R_{11}$ may include methyl, butyl, phenyl, p-butylphenyl, p-nonylphenyl, p-dimethylaminophenyl, p-diethylaminophenyl, p-(piperidino)phenyl, or the like.

Other examples of useful terminating reagents include tin tetrachloride, $(R_{11})_3SnCl$, $(R_{11})_2SnCl_2$, $R_{11}SnCl_3$, carbodiimides, N-methylpyrrolidine, cyclic amides, cyclic ureas, isocyanates, Schiff bases, 4,4'-bis(diethylamino) benzophenone, and the like, where $R_{11}$ is an alkyl, cycloalkyl or aralkyl having from 1 to about 12 carbon atoms, and other reactive hysteresis-reducing terminating compounds which may contain other heteroatoms such as oxygen, nitrogen, sulfur, phosphorus, tin, noninterfering halogen, etc. Suitable terminating reagents also include the isomeric vinylpyridines, dialkylaminobenzaldehydes, (bis) dialkylsminobenzophenones (Michler's ketones), dimethylimidazolidinone, etc. The living polymer may also be coupled with any of the various known coupling reagents, such as silicon tetrachloride, etc., to prepare symmetrically "dicapped" polymers. By the end-linking of polymers initiated with lithium hydrocarbon amides, through reaction with for example, $R_aSnY_b$, where R, Y, a and b are as described hereinabove; $SnCl_4$; or $C_4H_9SnCl_3$; to obtain products with substantially greater than 10 percent end-linking through tin, especially desirable elastomeric compositions with low hysteresis properties are prepared.

The terminating reagent is added to the reaction vessel, and the vessel is agitated for about 1 to about 1000 minutes. As a result, an elastomer is produced having an even greater affinity for compounding materials such as carbon black, and hence, even further reduced hysteresis. Additional examples of terminating reagents include those found in U.S. Pat. No. 4,616,069 which is herein incorporated by reference for the disclosure of terminating agents.

The polymer may be separated from the solvent by conventional techniques. These include steam or alcohol coagulation, thermal desolventization, or any other suitable method. Additionally, solvent may be removed from the resulting polymer by drum drying, extruder drying, vacuum drying or the like.

The elastomers made from the anionic initiators of the present invention comprise a plurality of polymer molecules, having a functional group at both the head, and preferably also, at the tail of the resulting polymer. Compounding such elastomers results in products exhibiting reduced hysteresis, which means a product having increased rebound, decreased rolling resistance and has less heat build-up when subjected to mechanical stress.

The polymers made from the anionic initiators of the present invention can be used alone or in combination with other elastomers to prepare a product such as a tire treadstock, sidewall stock or other tire component stock compound. Such stocks are useful for forming tire components such as treads, subtreads, black sidewalls, body ply skims, bead fillers and the like. At least one such component is produced from a vulcanizable elastomeric or rubber composition. For example, they can be blended with any conventionally employed treadstock rubber which includes natural rubber, synthetic rubber and blends thereof. Such rubbers are well known to those skilled in the art and include synthetic polyisoprene rubber, styrene/butadiene rubber (SBR), polybutadiene, butyl rubber, poly(chloroprene), ethylene/propylene rubber, ethylene/propylene/diene rubber (EPDM), acrylonitrile/butadiene rubber (NBR), silicone rubber, the fluoroelastomers, ethylene acrylic rubber, ethylene vinyl acetate copolymer (EVA), epichlorohydrin rubbers, chlorinated polyethylene rubbers, chlorosulfonated polyethylene rubbers, hydrogenated nitrile rubber, tetrafluoroethylene/propylene rubber and the like. When the polymers of the present invention are blended with conventional rubbers, the amounts can vary widely such as between 10 and 99 percent by weight.

The polymers can be compounded with carbon black in amounts ranging from about 20 to about 100 parts by weight, per 100 parts of rubber (phr), with about 40 to about 70 phr being preferred. The carbon blacks may include any of the commonly available, commercially-produced carbon blacks but those having a surface area (EMSA) of at least 20 $m^2/g$ and more preferably at least 35 $m^2/g$ up to 200 $m^2/g$ or higher are preferred. Surface area values used in this application are those determined by ASTM test D-1765 using the cetyltrimethyl-ammonium bromide (CTAB) technique. Among the useful carbon blacks are furnace black, channel blacks and lamp blacks. More specifically, examples of the carbon blacks include super abrasion furnace (SAF) blacks, high abrasion furnace (HAF) blacks, fast extrusion furnace (FEF) blacks, fine furnace (FF) blacks, intermediate super abrasion furnace (ISAF) blacks, semi-reinforcing furnace (SRF) blacks, medium processing channel blacks, hard processing channel blacks and conducting channel blacks. Other carbon blacks which may be utilized include acetylene blacks. Mixtures of two or more of the above blacks can be used in preparing the carbon black products of the invention. Typical values for surface areas of usable carbon blacks are summarized in the following TABLE I.

TABLE I

CARBON BLACKS

| ASTM Designation (D-1765-82a) | Surface Area ($m^2/g$) (D-3765) |
|---|---|
| N-110 | 126 |
| N-220 | 111 |
| N-339 | 95 |
| N-330 | 83 |
| N-550 | 42 |
| N-660 | 35 |

The carbon blacks utilized in the preparation of the rubber compounds used may be in pelletized form or an unpelletized flocculent mass. Preferably, for more uniform mixing, unpelletized carbon black is preferred. The reinforced rubber compounds can be cured in a conventional manner with known vulcanizing agents at about 0.5 to about 4 phr. For example, sulfur or peroxide-based curing systems may be employed. For a general disclosure of suitable vulcanizing agents one can refer to Kirk-Othmer, *Encyclopedia of Chemical Technology* 3rd ed., Wiley Interscience, N.Y. 1982, Vol. 20, pp. 365–468, particularly "Vulcanization Agents and Auxiliary Materials" pp. 390–402. Vulcanizing agents may be used alone or in combination.

Vulcanizable elastomeric compositions made from the above elastomers can be prepared by compounding or mixing the polymers thereof with carbon black and other conventional rubber additives such as fillers, plasticizers, antioxidants, curing agents and the like, using standard rubber mixing equipment and procedures and conventional amounts of such additives.

GENERAL EXPERIMENTAL

In order to demonstrate the preparation and properties of the initiators according to the present invention and their use in anionic polymerization, a number of such cyclic amino alkyllithium compounds were prepared. These compounds were then used as initiators to form a number of elastomers.

The aminoalkyllithium reagents of the invention may be prepared under a variety of conditions, using various hydrocarbon solvents as discussed hereinabove. The reagents may be used in polymerizations using such polar or nonpolar solvents as may be necessary for improved solubility of the aminoalkyllithium reagent, provided that the solvents are compatible with anionic polymerizations and the solvent recovery and polymer drying procedures.

In one preferred embodiment of the invention that provides for the production of reduced hysteresis polymers in substantially hydrocarbon solvents, such as hexane or cyclohexane, the initiator is hexamethyleneiminopropyllithium, which may be generated by at least two exemplary routes as is also discussed above: 1) by the reaction of a mixture of one equivalent of for example, 1-(N-hexamethyleneimino)-3-chloropropane with about two atom equivalents of lithium metal; or 2) a "one-pot" generation of for example, hexamethyleneiminopropyllithium, wherein 1-bromo-3-chloropropane is treated with N-lithiohexamethyleneimine, and the product 1-(N-hexamethyleneimino)-3-chloropropane is then treated in situ with two equivalents of t-butyllithium. The reactions are preferably performed in hexanes, cyclohexane, benzene, or mixtures thereof.

The amino alkyllithium reagents of the invention may be formed in a solvent or solvent mixture, and then transferred to another solvent or solvent mixture for use in a polymerization reaction.

The initiators of this invention may optionally be treated with from about one to 500 equivalents of a monomer such as butadiene or isoprene, before the main (co) polymerization charge is made, although this is not required. Polymers according to the invention can be prepared with a relatively narrow molecular weight range distribution, with a substantial fraction of living C—Li chain ends adaptable to further functionalization or coupling, being obtained.

The initiator formation, polymerization, and coupling and/or termination may be performed in one reaction vessel, or second or third reactor vessels, or transfer lines from the original reactor can be used, by introducing the preformed initiator to the monomer mixture, or vice-versa. Polymerization and post-treatment conditions should be used that avoid the introduction of air and/or protic or other reactive contaminants, such as moisture, etc., and prolonged heating or storage at excessive temperatures should be avoided unless the live ends are stabilized. Low to high temperatures (from about −70° C. to about 200° C.) are useful for the polymerizations and the terminations. Polymerization and post-treatment temperatures of from about 15° C. to 125° C. are preferred. The polymerization time may vary from a few minutes to days, depending on the temperature, solvent and presence of any donor solvent, the monomer structures, and the molecular weight desired.

Any suitable method for isolation of the terminated rubber or fluid may be used, for example: quenching with water, steam, an acid or an alcohol (these may be introduced during the desolventization step), and desolventization by drum drying, coagulation in alcohol, water or steam, extruder drying, vacuum drying, spray drying or any combination thereof. Desolventization by drum-drying, coagulation in alcohol, steam or hot water desolventization, extruder drying, vacuum drying, spray drying or combinations thereof are preferred. An antioxidant and/or antiozonant compound is usually added to the polymer or polymer cement at or before this stage. In most of the experimental examples of this invention, alcohol coagulation followed by drum-drying or vacuum drying were used.

Upon drying, the elastomers are compounded in a carbon black-filled test stock (see Low-Oil Test Recipe, TABLE II), and the physical properties determined in comparison to those of related base polymers without the modifications. In practice, a wide variety of compounding recipes may be used to give favorable results with this invention, although hysteresis properties may vary from formulation to formulation, depending on the type and amount of carbon black and oil used, and so on. Certain other fillers, such as silica or hydrated silica may also be useful. Furthermore, the polymers made with the initiators of this invention may be combined in proportions of 20 to 100 percent by weight with 80 to 0 percent by weight of other polymers to give elastomeric compositions with reduced hysteresis loss characteristics. The low molecular weight products made from the initiators of this invention may be used at low levels to influence the properties of mixtures with other fluids and/or particulates.

TABLE II

LOW-OIL TEST FORMULATION FOR EVALUATION OF HYSTERESIS

| Ingredient | Mix Order | Parts per Hundred Parts of Rubber |
|---|---|---|
| Polymer | 1 | 100 |
| Naphthenic oil | 2 | 10 |
| Carbon black, N-351 | 3 | 55 |
| ZnO | 4 | 3 |
| Antioxidant | 5 | 1 |
| Wax blend | 6 | 2 |
| Total Masterbatch: | | 171 |
| Stearic acid | | 2 |
| Sulfur | | 1.5 |
| Accelerator | | 1 |
| Total Final: | | 175.5 |

Masterbatch: 145°–155° C., 60 RPM (drop after 5 min, @ 155°–175° C.)
Final: 77°–95° C., 40 RPM The following preparations exemplify the invention.

EXAMPLE 1

A "One-Pot" Preparation of Hexamethyleneiminopropyllithium

The (bis)tetrahydrofuran N-lithio salt of hexamethyleneimine was prepared in hexane. Equimolar amounts of this salt and 1-chloro-3-bromopropane (5 mmol+5 mmol) were mixed in hexanes at about −25° C., and the mixture was allowed to warm to about 0° C. while swirling over 45 minutes. The mixture was cooled to −25° C. again, and 10 mmol of t-butyllithium in pentane was added. The resulting mixture was allowed to warm slowly to room temperature and agitated gently overnight before use. It was estimated that 0.28M active Li was present and 0.24M, with 0.34M total base, was found. The mixture was used to initiate the polymerization of butadiene and styrene as described in the following examples.

EXAMPLE 2

Polymerizations of Styrene/Butadiene Mixtures Using Hexamethyleneiminopropyllithium Polymerizations were run using the initiator solution prepared according to Example 1 hereinabove. The following table (TABLE III) lists the ingredients and conditions used in the polymerizations. A 0.24M solution of the above initiator was added to a dried, sealed, nitrogen-purged bottle, through a Viton rubber cap liner, to a 75 percent/25 percent by weight blend of butadiene and styrene in hexanes, at an estimated level of 0.75 milliequivalent ("mequiv.") active C-Li/100 grams monomer, and an additional amount of N,N,N',N'-tetramethylethylenediamine ("TMEDA") was added at the TMEDA/Li ratio indicated in TABLE III.

TABLE III

POLYMERIZATION OF STYRENE/BUTADIENE

| | SAMPLE A | SAMPLE B |
|---|---|---|
| Amount (g) of Monomer | 90.6 | 95.3 |
| ml of 2.0M TMEDA (TMEDA/Li) | 0.42 | 0.43 |
| | (1:1) | (1:1) |

TABLE III-continued

POLYMERIZATION OF STYRENE/BUTADIENE

| | SAMPLE A | SAMPLE B |
|---|---|---|
| Initiator, mequiv | 0.82 | 0.86 |
| Initiator, ml | 2.91 | 3.06 |
| Pzn temperature, °C. | 80 | 80 |
| Pzn time, minutes | 40 | 40 |

The mixtures were agitated at 80° C. for 0.5 to 2.5 hours ("hr"), proceeding to approximately 94–98 percent conversion to polymer. In practice, there is considerable leeway in the reaction times and temperatures, much the same as there is leeway in the reaction vessels, type of agitation, etc., used. The treated cements then were quenched by injection with 1.5 ml of i-PrOH (isopropyl alcohol), treated with an antioxidant (3 ml of a mixture containing 1.6 wt % dibutyl paracresol (DBPC) in hexane), coagulated in i-PrOH, air-dried at room temperature, then drum-dried. Suitable characterization tests were performed. Analyses of the product polymer are given in TABLE IV (Run A).

EXAMPLE 3

Polymerizations of Styrene/Butadiene Mixtures Using Hexamethyleneiminopropyllithium and End-Linking With $SnCl_4$ The procedure of Example 2 was followed, except that after 40 minutes of polymerization at 80° C., the polymerization mixture was treated with 0.8 equiv. of $SnCl_4$ per equivalent ("equiv.") of Li charged. The mixture was agitated at 50° C. for 30 minutes. The product was isolated and dried in the same manner as above. It showed about 40 percent coupling in the 80° C. polymerization. Analyses of this polymer are also given in TABLE IV (Run B).

TABLE IV

ANALYSIS OF COMPOUNDED POLYMERS

| RUN: | SAMPLE A | SAMPLE B |
|---|---|---|
| Polymer recovered % | 94 | 95 |
| tan δ, °C. (DSC, onset) | −43.9 | −44.2 |
| ML/4/100, raw | 62.4 | 96.2 |
| GPC (THF): | | |
| $M_n$ | 202762 | 248129 |
| $M_w/M_n$ | 1.25 | 1.94 |

EXAMPLE 4

Compounded Evaluations of Polymers Made From Hexamethyleneiminopropyllithium

The product polymers (from Runs A and B of Table IV) were compounded and tested as indicated in the test recipe shown in TABLE II, and cured 20 min @ 165° C. Compared to the control polymer, the results of the compounded evaluations are summarized in TABLE V. A control polymer, (a tin-coupled styrene/butadiene rubber ("SBR") initiated with t-butyllithium) was also compounded and tested. Compared to the control polymer, the product of Run A exhibited improved hysteresis loss characteristics and enhanced interaction with carbon black, compared to unmodified elastomers of the same molecular weight embodied in the control polymer. In these experiments, the polymers were of higher molecular weight than anticipated, since the initiator was part of a mixture.

TABLE IV

POLYMER ANALYSIS

| Feature | Polymer Sample i[a] | Polymer Sample A[b] | Polymer Sample B[c] |
|---|---|---|---|
| | Sn-Coupled Control (BuLi[d] initiator) | HMI—Pr—Li[e] 80° C. | HMI—Pr—Li 80° C./SnCl$_4$ |
| ML/4-Raw | 74 | 62.4 | 96.2 |
| ML/4-Cpd | 67.3 | 107.1 | 116.1 |
| #1 Dispersion Index % | 95.0 | 89.9 | 76.7 |
| Dynastat 1 Hz, tan δ, 50° C. | 0.0934 | 0.0895 | 0.0926 |

[a]Control SBR
[b]Inventive polymer prepared according to Example 2
[c]Inventive polymer prepared according to Example 3
[d]butyllithium
[e]Hexamethyleneimine propyllithium It is clear from the foregoing examples and specification disclosure, that the present invention provides novel cyclic aminoalkyllithium compounds useful for example, as anionic polymerization initiators for the preparation of diene monomers. Reproducible polymerization of such polymers within a relatively narrow molecular weight range is achieved, and the resulting polymers also exhibit good preservation of live C—Li ends which permits further polymer functionalization through the use of terminating reagents.

It is to be understood that the invention is not limited to the specific initiator reactants, monomers, terminators, polar coordinators or solvents disclosed herein, except as otherwise stated in the specification. Similarly, the examples have been provided merely to demonstrate practice of the subject invention and do not constitute limitations of the invention. Those skilled in the art may readily select other monomers and process conditions, according to the disclosure made hereinabove.

Thus, it is believed that any of the variables disclosed herein can readily be determined and controlled without departing from the scope of the invention herein disclosed and described. Moreover, the scope of the invention shall include all modifications and variations that fall within the scope of the attached claims.

What is claimed is:

1. An organolithium compound having the formula:

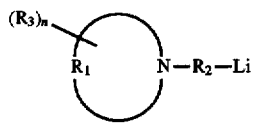

wherein the moiety

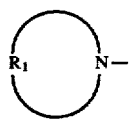

is a cyclic amino group where $R_1$ is a divalent alkylene group that has from 6 to about 20 carbon atoms; $R_2$ is a linear-, branched-, or cyclo-alkylene having from about 2 to about 20 carbon atoms; $R_3$ is selected from the group consisting of a tertiary amino group having from 1 to about 12 carbon atoms, an alkyl group having from 1 to about 12 carbon atoms, an aryl group having from about 6 to about 20 carbon atoms, an aralkyl group having from about 7 to about 20 carbon atoms, an alkenyl group having from about 2 to about 12 carbon atoms, a cycloalkyl group having from about 5 to about 20 carbon atoms, a cycloalkenyl group having from about 5 to about 20 carbon atoms, a bicycloalkyl group having from about 6 to about 20 carbon atoms, and a bicycloalkenyl group having from about 6 to about 20 carbon atoms, n is an integer of from 0 to about 10; and the lithium, Li, is bonded directly to a carbon atom of $R_2$.

2. An organolithium compound, as set forth in claim 1, where $R_1$ has from about 6 to about 12 carbon atoms.

3. An organolithium compound, as set forth in claim 1, where $R_2$ has from about 3 to about 12 carbon atoms.

4. An organolithium compound, as set forth in claim 1, where n is an integer from 1 to 10.

5. An anionic polymerization initiator for the polymerization of diene polymer and copolymer elastomers having reduced hysteresis loss characteristics, comprising:

a cyclic amine compound having the formula:

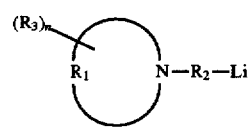

wherein the moiety

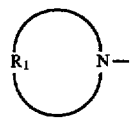

is a cyclic amine group where $R_1$ is a divalent alkylene group that has from 6 to about 20 carbon atoms; and, $R_2$ is a linear-, branched-, or cyclo-alkylene having from about 2 to about 20 carbon atoms; $R_3$ is selected from the group consisting of a tertiary amino group having from 1 to about 12 carbon atoms, an alkyl group having from 1 to about 12 carbon atoms, an aryl group having from about 6 to about 20 carbon atoms, an aralkyl group having from about 7 to about 20 carbon atoms, an alkenyl group having from about 2 to about 12 carbon atoms, a cycloalkyl group having from about 5 to about 20 carbon atoms, a cycloalkenyl group having from about 5 to about 20 carbon atoms, a bicycloalkyl group having from about 6 to about 20 carbon atoms, and a bicycloalkenyl group having from about 6 to about 20 carbon atoms, n is an integer of from 0 to about 10, and the lithium, Li, is bonded directly to a carbon atom of $R_2$.

6. An anionic polymerization initiator, as set forth in claim 5, where $R_1$ has from about 6 to about 12 carbon atoms.

7. An anionic polymerization initiator, as set forth in claim 5, where $R_2$ has from about 3 to about 12 carbon atoms.

8. An anionic polymerization initiator, as set forth in claim 5, where n is an integer from 1 to 10.

* * * * *